US007419789B2

(12) United States Patent
Amara et al.

(10) Patent No.: US 7,419,789 B2
(45) Date of Patent: Sep. 2, 2008

(54) METHOD OF INHIBITING BINDING OF DENGUE VIRUS TO A HUMAN CELL WITH DC-SIGN BLOCKERS

(75) Inventors: Ali Amara, Paris (FR); Fernando Arenzana-Seisdedos, Nevron (FR); Philippe Despres, La Garenne-Colombes (FR); Jean-Louis Virelizier, Paris (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 10/700,491

(22) Filed: Nov. 5, 2003

(65) Prior Publication Data

US 2004/0197330 A1      Oct. 7, 2004

Related U.S. Application Data

(60) Provisional application No. 60/425,246, filed on Nov. 12, 2002, provisional application No. 60/423,582, filed on Nov. 5, 2002.

(51) Int. Cl.
 *G01N 33/53* (2006.01)
 *A61K 39/12* (2006.01)
(52) U.S. Cl. .................................. 435/7.1; 424/218.1
(58) Field of Classification Search ............... 435/5, 435/7.1, 7.2, 7.94, 325, 363, 366; 424/130.1, 424/141.1, 159.1, 208.1, 218.1
See application file for complete search history.

(56) References Cited

U.S. PATENT DOCUMENTS

| 4,522,811 | A |   | 6/1985  | Eppstein et al. |
| 4,683,195 | A |   | 7/1987  | Mullis et al. |
| 4,683,202 | A |   | 7/1987  | Mullis |
| 5,223,409 | A |   | 6/1993  | Ladner et al. |
| 5,403,484 | A |   | 4/1995  | Ladner et al. |
| 5,498,538 | A |   | 3/1996  | Kay et al. |
| 5,516,637 | A |   | 5/1996  | Huang et al. |
| 5,565,332 | A | * | 10/1996 | Hoogenboom et al. ..... 435/69.1 |
| 5,571,698 | A |   | 11/1996 | Ladner et al. |
| 5,625,033 | A |   | 4/1997  | Kay et al. |
| 5,658,727 | A |   | 8/1997  | Barbas et al. |
| 5,667,988 | A |   | 9/1997  | Barbas et al. |
| 6,165,477 | A | * | 12/2000 | Ivy et al. ................. 424/218.1 |
| 6,391,567 | B1 | * | 5/2002  | Littman et al. ............... 435/7.2 |

FOREIGN PATENT DOCUMENTS

| EP | 1046651 A1 | * | 10/2000 |
| WO | WO 91/05876 A1 |   | 5/1991 |
| WO | WO 93/01820 |   | 2/1993 |
| WO | WO 00/63251 |   | 10/2000 |
| WO | WO 01/64752 A2 |   | 9/2001 |
| WO | WO 02/080851 A2 |   | 10/2002 |

OTHER PUBLICATIONS

Desrosiers, R. Prospects for an AIDS vaccine, Nature Medicine, 2004, 10(3):221-223.*
Feinburg et al. AIDS vaccine models: challenging challenge viruses, Nature Medicine, 2002, 8(3):207-210.*
Greene, W. The brightening future of HIV therapeutics, Nature Immunology, 2004, 5(9):867-871.*
Leyssen et al. Perspectives for the Treatment of Infections with Flaviviridae, Clinical Microbiology Reviews, 2000, 13(1):67-82.*
Centers for Disease Control Dengue Fever Home Page, website last updated 2003 http://www.cdc.gov/ncidod/dvbid/dengue/index.htm.*
Tassaneetrithep et al. DC-SIGN (CD209) mediates dengue virus infection of human dendritic cells, Journal of Experimental Medicine, Apr. 2003, 197(7):823-829.*
Men et al. Identification of Chimpanzee Fab Fragments, Journal of Virology, 2004, 78(9):4665-4674.*
Brandriss et al. Lethal 17D Yellow Fever Encephalitis in Mice, Journal of General Virology, 1986, 67:229-234.*
Curtis, Benson M. et al., "Sequence and Expression of a Membrane-Associated C-type Lectin that Exhibits CD4-Independent Binding of Human Immunodeficiency Virus Envelope Glycoprotein gp120," *Proc. Natl. Acad. Sci. USA*, vol. 89, pp. 8356-8360 (1992).
Geijtenbeek, Teunis B.H. et al., "Identification of DC-Sign, a Novel Dendritic Cell-Specific ICAM-3 Receptor that Supports Primary Immune Responses," *Cell*, vol. 100, pp. 575-585 (2000).
Halary, Franck et al., "Human Cytomegalovirus Binding to DC-Sign is Required for Dendritic Cell Infection and Target Cell *trans*-Infection," *Immunuty*, vol. 17, pp. 653-664 (2002).
Tailleux, Ludovic et al., "DC-Sign is the Major Mycobacterium Tuberculosis Receptor on Human Dendritic Cells," *The Journal of Experimental Medicine*, vol. 197, pp. 121-127 (2003).
Desrosiers, R., "Prospects for an AIDS Vaccine," *Nature Medicine*, 10(3):221-233 (2004).
Feinberg et al, "AIDS Vaccine Models: Challenging Challenge Viruses," *Nature Medicine*, 9(3):207-210 (2002).

(Continued)

*Primary Examiner*—Stacy B Chen
(74) *Attorney, Agent, or Firm*—Finnegan, Henderson, Farabow, Garrett & Dunner, L.L.P.

(57) ABSTRACT

The present invention relates to methods and compositions for preventing or treating diseases of a mammal, including viral infections, wherein at least one symptom of the disease is mediated at least in part by the binding of an effector molecule to a DC-SIGN receptor present on cells of the mammal to be treated. The invention also provides methods of identifying compositions, wherein the compositions are useful for treating mammalian diseases, including viral infections, for which at least one symptom of the disease is mediated at least in part by the specific binding of an effector molecule to a DC-SIGN receptor present on the cells that express the DC-SIGN receptor, belonging to the mammal to be treated. The invention further relates to compositions and methods for targeting subject molecules to cells that express the DC-SIGN receptor.

3 Claims, 8 Drawing Sheets

OTHER PUBLICATIONS

Greene, W., "The Brightening Future of HIV Therapeutics," *Nature Immunology*, 4(9):867-871 (2004).

Halary et al.; "Human Cytomegalovirus Binding to DC-Sign is Required for Dendritic Cell Infection and Target Cell *Trans-Infection*"; Immunity, vol. 17, No. 5, pp. 653-664, (2002).

Kwon et al.; "DC-Sign-Mediated Internalization of HIV is Required for *Trans*-Enhancement of T Cell Infection"; *Immunity*, vol. 16, No. 1, pp. 135-144, (2002).

MacDonald et al., "Mucosal and Parenteral Vaccination Against Acute and Latent MCMV," *J. Virology*, 72(1):442-451 (1998).

Navarro-Sanchez et al.; "Dendritic-Cell-Specific ICAM3-Grabbing Non-Integrin is Essential for the Productive Infection of Human Dendritic Cells by Mosquito-Cell-Derived Dengue Viruses"; EMBO Reports, vol. 4, No. 7, pp. 723-728, (2003).

Tassaneetrithep et al.; "DC-Sing (CD209) Mediates Dengue Virus Infection of Human Dendritic Cells"l Journal of Experimental Medicine, vol. 197, No. 7, pp. 823-829, (2003).

Wang et al., Recombinant Modified Vaccinia Virus Ankara Expressing a Soluble Form of Glycoprotein B, *J. Virology*, 78(8):3965-3976 (2004).

Office Action dated Dec. 28, 2004 in U.S. Appl. No. 10/700,507.

Office Action dated Oct. 17, 2005 in U.S. Appl. No. 10/700,507.

U.S. Appl. No. 10/464,531 of Olivier Neyrolles, Olivier Schwartz, Ludovic Tailleux , and Phillippe LaGrange, filed Jun. 19, 2003.

U.S. Appl. No. 10/700,507 of Ali Amara, Frank Halary, Julie Dechanet-Merville, Jean-Francois Moreau, Fernando Arenzana-Seisdedos and Thierry Delaunay, filed Nov. 5, 2003.

WO 2004/041299 A1 published May 21, 2004, which entered the National Stage in U.S. Appl. No. 10/533,924.

Office Action mailed Jun. 26, 2006, in U.S. Appl. No. 10/700,507, which was filed Nov. 5, 2003.

* cited by examiner

DEN-1 virus-infected DCs

DEN-1 virus-infected DCs

Viral antigens     Apoptotic nuclei human Dendritic cells
DEN-1 virus strain FGA/NA d1d (m.o.i. 5)

anti-DEN-1 E protein anti-DC-SIGN

MAb 9D12    MAb 1B10    No Ab vAg-positive cells (%)

FIA: 42 h post-infection

Figure 3

**THP-1/DC-SIGN
DEN-1 virus
m.o.i. 5**

**THP-1/DC-SIGN
Mutant 35
DEN-1 virus
m.o.i. 5**

METHOD OF INHIBITING BINDING OF DENGUE VIRUS TO A HUMAN CELL WITH DC-SIGN BLOCKERS

PRIORITY INFORMATION

Applicants claim the right to priority under 35 U.S.C. § 119(e), based on Provisional Patent Application Nos. 60/423,582, filed Nov. 5, 2002, and 60/425,246, filed Nov. 12, 2002, both of which are incorporated herein by reference in their entirety.

BACKGROUND OF THE INVENTION

1. Field of the Invention

This invention relates to methods and compositions for preventing or treating diseases of a mammal, wherein at least one symptom of the disease is mediated at least in part by the binding of an effector molecule to a DC-SIGN receptor of the mammal to be treated. The effector molecule may be a molecule on a foreign organism. The foreign organism may be a virus.

The invention also relates to compositions, and to methods of identifying compositions, wherein the compositions are useful for treating mammalian diseases for which at least one symptom of the disease is mediated at least in part by the binding of an effector molecule to a DC-SIGN receptor of the mammal to be treated.

The invention further relates to compositions and methods for targeting subject molecules to cells expressing DC-SIGN receptors, such as dendritic cells. These compositions and methods are based on targeting complexes, in which one or more subject molecules are covalently attached to one or more DC-SIGN blockers and, by virtue of binding of one or more of the DC-SIGN blockers of the targeting complex to DC-SIGN, the subject molecule is targeted to cells expressing DC-SIGN receptors.

2. Description of the Related Art

Dengue is an acute febrile tropical disease and the virus which causes it is an arbovirus which is transmitted by mosquitoes. The vectors of the disease are mosquitoes of the *Aedes* genus, in particular *Aedes aegypti*, which most commonly leave their larvae in domestic and peridomestic areas. The responsible virus, isolated in 1951, has been classified into four different antigenic types (DEN1, DEN2, DEN3 and DEN4). It belongs to the Flaviviridae family, genus *flavivirus*.

More than two billion inhabitants live in endemic regions and the number of individuals infected by the virus is thought to be more than 100 million per year. Dengue is in particular responsible for 500 000 hospitalizations and for several tens of thousands of deaths annually, mostly children.

After an incubation of five to eight days, the clinical signs generally begin suddenly and consist of the appearance of undifferentiated fever (DF dengue fever) accompanied by severe headaches, lumbago, muscle and joint pain and also shivering. From the third to the fifth day of the febrile phase, a congestive maculopapular rash may appear for three to four days (conventional dengue).

In its severe form, the infection may result in the appearance of a hemorrhagic-syndrome (DHF or dengue hemorrhagic fever), characterized by increased vascular permeability and deregulation of hemostasis. Although, in the majority of cases, the disease generally evolves favorably within a week, it may turn out to be fatal in the event of hypovolemic shock (DSS or dengue shock syndrome). These complications may be due to the presence of preexisting immunity, acquired in particular during a primary infection with a heterologous dengue virus (different serotype). Specifically, two different types of serological response are identified in individuals infected with dengue: individuals who have never suffered a *flavivirus* infection and have not been vaccinated, against another *flavivirus* (yellow fever virus, Japanese encephalitis virus for example) will exhibit a primary response, characterized by a slow appearance of antibodies specific for the virus responsible for the infection; individuals who have already suffered a *flavivirus* infection (other dengue serotype for example) or have been vaccinated against another *flavivirus* will exhibit a secondary response, characterized by the rapid appearance of antibodies.

The infectious agent is the dengue virus which belongs to the Flaviviridae family, to which the yellow fever virus and the Japanese encephalitis virus also belong (T. P. Monath et al., (1996) *Flaviviruses* in B. N. Fields, D. M. Knipe, P. M. Howly et al. (eds.) "Fields Virology" Philadelphia: Lippincott Raven Press Publishers). These viruses have a single-strand RNA with positive polarity which comprises 11 000 nucleotides and which encodes a polyprotein of approximately 3400 amino acids. It is separated into three structural proteins and seven nonstructural proteins NS1, NS2A, NS28, NS3, NS4A, NS4B and NS5, during co-translational and post-translational cleavage by viral and cellular proteases. The NS1 nonstructural protein was identified for the first time in 1970 by P. K. Russel et al. (J. Immunol., (1970), 105, 838-845) and characterized in 1985 by G. W. Smith et al. (J. Gen Virol., (1985), 66, 559-571). This glycoprotein, which is highly conserved in the *flavivirus* genus (T. P. Monath already mentioned), in particular in the four dengue virus serotypes, exists in an intracellular form and in an extracellular form. The intracellular form is thought to be involved in the early phases of replication of the virus (Hall R. A. et al., *J. Virol.* (1999), 73, 10272-10280; Rice C. M. at al., *J. Virol.*, (1997), 71, 291-298; Rice C. M. et al., *J. Virol.*, (1996), 222, 159-168; Rice C. M. et al., *J. Virol.*, (1997), 71, 9608-9617). Before being transported to the plasma membrane, the NS1 protein undergoes dimerization. In mammalian cells, but not in insect cells, a portion of the NS1 protein is released into the extracellular medium, either primarily in the form of a soluble protein, or secondarily in a microparticulate form. When it is in a soluble form, the protein exists in the form of an oligomer, in particular of a pentamer or of a hexamer (Crooks A. J. et al. J. Chrom. (1990), 502, 59-68 and *J. Gen. Virol.* (1994), 75, 3453-3460 and Glamand et al., J. Virol. (1999), 73, 6106-6110).

No specific treatment exists and the care given to the patient is uniquely symptomatic. In the case of conventional dengue, the treatment is based on the administration of analgesics and antipyretics. In the case of DHF, the treatment consists of an infusion to compensate for the plasma leakage, combined with correction of hydroelectric problems and reinitiation of diuresis.

There is no commercially available vaccine against the dengue virus. On the other hand, protection assays with attenuated strains of the 4 dengue virus serotypes have been carried out by N. Bhamarapravati et: al. (*Dengue and Dengue haemorrhagic fever* (1997), 367-377), with unsatisfactory results. Prevention is therefore based solely on combating the vector. This combat combines larval destruction and "adulticide" spraying.

The pathogenesis of severe forms of dengue (DEN) virus infection is not completely understood. Substantial T cell activation is observed in severe DEN disease. A number of cytokines and chemokines are found to be elevated in dengue hemorrhagic fever and/or dengue shock syndrome. Macrophages have long been recognized as an important component of DEN pathogenesis. As emphasized by Palucka, immature human dendritic cells (DC), in contrast to other leukocytes, were preferentially permissive for DEN infection (Wu et al., *Nat. Med.* 6:816, 2000; for review: Palucka, *Nat. Med* 6: 748, 2000). Unlike monocytes/macrophages, DEN virus infection was not enhanced by specific antibody (Marovich et al., *JID Symp. Proc.* 6:219, 2001). Immature DCs can undergo maturation in response to DEN virus infection. Upregulation of surface markers B7-1, B7-2, HLA-DR CD11b and DC83 and cytokine production were observed following infection of DCs. There is growing evidence that DEN infection can induce functional maturity in DC. Such infection causes upregulation of surface markers B7-1, B7-2, HLA-DR CD11b and DC83 and stimulates cytokine production (Ho et al., *Immunology* 166: 1499, 2001). Immature DCs exposed to DEN virus produce TNF-$\alpha$, which may perturb endothelial cell function.

Dendritic cells (DC) are specialized Antigen Presenting Cells (APC) involved in the initiation of T cell-dependent immune responses as consequence of their high expression of MHC and costimulatory molecules. Myeloid DC are distributed throughout the body in an immature state, exhibiting a high capacity for antigen uptake and processing. Once activated by inflammatory stimuli or infectious agents, DC undergo a maturation process, migrate to lymphoid organs, and acquire their capacity to activate naive T lymphocytes.

An important question is which of DC-specific molecules DEN virus uses as a receptor for entry. The human DC-specific adhesion receptor DC-SIGN (ICAM-grabbing non integrin or CD-209), a type 11 integral protein, is of particular interest because its expression is largely restricted to immature DCs. DC-SIGN has been shown to be the ligand of ICAM-3, which enables transient DC-T cell interactions, thus facilitating primary immune response (Geijtenbeek et al. *Nature* 1: 353, 2000). DC-SIGN appeared to be a critical mediator of the migratory and T cell-interacting capabilities exhibited by maturing immature myeloid monocyte-derived DCs. DC-SIGN expression is IL-4 dependent and is negatively regulated by IFN-$\gamma$, IFN-$\gamma$, TGF-$\beta$, and anti-inflammatory agents (Relloso et al., *J. Immunol.* 168: 2634, 2002). DC-SIGN polymorphisms might also explain why some patients mount protective immunity whereas other do not.

DC-SIGN, a C-type lectin, has a single carbohydrate recognition domain that interacts with proteins with either mannose or galactose side chains in a calcium-dependent manner (Drickammer, *Curr. Opin. Immunol.* 13: 585, 1999). DC-SIGN is now believed to bind to high-mannose oligosaccharides that are present on the viral glycoproteins and thereby may capture enveloped viruses (Feinberg et al., *Science* 294: 2163, 2001). For example, DC-SIGN binds to the HIV envelope glycoprotein gp120 (Geijtenbeek et al. *Cell,* 100: 587, 2000) and thereby mediates rapid internalization of intact HIV into a nonlysosomal compartment (Kwon et al., *Immunity,* 16: 135, 2002).

There exists a need in the art to develop methods and compositions for modulating the specific binding of effector molecules to the DC-SIGN receptor, for example on the dendritic cells of mammals. Such methods and compositions are needed, for example, to prevent and treat diseases such as viral infections; for example Dengue virus infections. In this regard, there is a need to identify cell proteins involved in viral attachment and/or fusion. Additionally, methods and compositions are needed that allow the specific targeting of cells expressing DC-SIGN receptor, such as dendritic cells or alveolar macrophages, to aid in therapy or diagnosis.

SUMMARY OF THE INVENTION

The inventors sought to determine whether the DC-specific adhesion receptor DC-SIGN has the ability to promote DEN virus infection of human DC cells. The data reported herein showed that DC-SIGN specific antibodies have a blocking action at the level of DEN-1 virus infection. These results establish a novel function of DC-SIGN, as a Dengue virus binding protein, likely through interaction with the E glycoprotein. The process of DC-SIGN-mediated Dengue virus infectivity to DCs provides a new mechanism for targeting the design of anti-viral compounds.

Accordingly, this invention identifies DC-SIGN as a receptor involved in the binding of viruses other than HIV to dendritic cells. The invention further provides a number of novel methods and compositions for treating diseases of mammals, including viral infections.

A first object of the invention is to provide a method of preventing or treating a disease of a mammal, where at least one symptom of the disease is mediated at least in part by the binding of an effector molecule to a DC-SIGN receptor of the mammal to be treated, and where the method comprises administering to the mammal an amount of a DC-SIGN modulator sufficient to substantially modulate the binding of the effector molecule to the DC-SIGN receptor to thereby prevent or treat the disease.

Another object of the invention is to provide a method of preventing or treating a disease of a mammal, where at least one symptom of the disease is mediated at least in part by the binding of an effector molecule to a DC-SIGN receptor of the mammal to be treated, and where the method comprises administering to the mammal an amount of a DC-SIGN blocker sufficient to substantially inhibit the binding of the effector molecule to the DC-SIGN receptor to thereby prevent or treat the disease.

In some embodiments the DC-SIGN blocker is a blocking derivative of the effector molecule. In other embodiments the DC-SIGN blocker is an antibody.

Among embodiments of the invention where the DC-SIGN blocker is an antibody are included embodiments where the antibody specifically binds DC-SIGN and embodiments where the antibody specifically binds the effector molecule.

In some embodiments the DC-SIGN blocker is a mannosylated molecule that binds to a DC-SIGN receptor. The mannosylated molecule may be mannan.

A further object of the invention is to provide a method of preventing or treating a viral infection of a mammal, where the viral infection is mediated at least in part by the binding of a viral effector molecule to a DC-SIGN receptor of the mammal to be treated, where the method comprises administering to the mammal an amount of a DC-SIGN modulator sufficient to substantially modulate the binding of the viral effector molecule to the DC-SIGN receptor to thereby prevent or treat the viral infection.

Another object of the invention is to provide a method of preventing or treating a viral infection of a mammal, where the viral infection is mediated at least in part by the binding of a viral effector molecule to a DC-SIGN receptor of the mammal to be treated, where the method comprises administering to the mammal an amount of a DC-SIGN blocker sufficient to substantially inhibit the binding of the viral effector molecule to the DC-SIGN receptor to thereby prevent or treat the viral infection.

In some embodiments of the method the DC-SIGN blocker comprises a binding moiety of the viral effector molecule. In other embodiments the DC-SIGN blocker comprises a binding moiety of a viral envelope glycoprotein. In other embodiments the DC-SIGN blocker is an antibody. The antibody may specifically bind DC-SIGN or specifically bind the viral effector molecule. In additional embodiments the DC-SIGN blocker is a mannosylated molecule that binds to a DC-SIGN receptor. The mannosylated molecule may be mannan.

Among embodiments of the invention in which the DC-SIGN blocker is an antibody are included embodiments in which the antibody is a monoclonal antibody; the mammal is a human and the antibody is a monoclonal antibody that is humanized; the antibody specifically binds DC-SIGN; the monoclonal antibody is Mab 1B10.2.6; the antibody specifically binds the viral effector molecule; and the antibody specifically binds the binding moiety of the viral effector molecule.

In further embodiments of the method the viral effector molecule is a molecular constituent of the viral envelope. In certain embodiments the molecular constituent of the viral envelope is an envelope glycoprotein.

In additional embodiments of the method the DC-SIGN blocker comprises a binding moiety of the viral effector molecule. In some embodiments of the invention in which the viral effector molecule is a molecular constituent of the viral envelope the DC-SIGN blocker that is used comprises a binding moiety of the envelope glycoprotein.

In a preferred aspect of the invention the viral infection is a Flaviviridae infection and the viral effector molecule is a Flaviviridae effector molecule. In a more preferred embodiment, the viral infection is a Dengue virus infection and the viral effector molecule is a Dengue virus effector molecule. In a further preferred aspect the mammal is a human. In some embodiments the Dengue virus effector molecule is a molecular constituent of the Dengue virus envelope. In further embodiments the molecular constituent of the Dengue virus envelope is a Dengue virus envelope glycoprotein. In yet further embodiments the Dengue virus envelope glycoprotein is Dengue virus E glycoprotein.

Included among embodiments of the invention in which the viral infection is a Dengue virus infection and the viral effector molecule is a Dengue virus effector molecule are embodiments where the DC-SIGN blocker comprises a binding moiety of the Dengue virus effector molecule; the DC-SIGN blocker comprises a binding moiety of the Dengue virus E glycoprotein; the DC-SIGN blocker is a recombinantly produced protein; and the DC-SIGN blocker is an antibody. Among embodiments where the DC-SIGN blocker is an antibody are embodiments where the antibody is a monoclonal antibody; the mammal is a human and the monoclonal antibody is humanized; the antibody specifically binds DC-SIGN; the monoclonal antibody is Mab 1B10.2.6; and the antibody specifically binds the Dengue virus effector molecule. Among embodiments where the antibody specifically binds the Dengue virus effector molecule are embodiments where the Dengue virus effector molecule is Dengue virus E glycoprotein.

In a further aspect the invention provides a method of preventing or treating an HIV or SIV infection of a human or a simian, where the method comprises administering to the human or simian an amount of a DC-SIGN modulator sufficient to substantially modulate the binding of HIV or SIV to the DC-SIGN receptor present on dendritic cells of the human or simian to thereby prevent or treat the HIV or SIV infection.

In another aspect the invention provides a method of preventing or treating an HIV or SIV infection of a human or a simian, where the method comprises administering to the human or simian an amount of a DC-SIGN blocker sufficient to substantially inhibit the binding of HIV or SIV to the DC-SIGN receptor present on dendritic cells of the human or simian to thereby prevent or treat the HIV or SIV infection. In a preferred embodiment the DC-SIGN blocker comprises a binding moiety of the Dengue virus E glycoprotein. In another preferred embodiment an HIV infection of a human is prevented or treated.

In a further aspect the invention provides a method of preventing or treating inflammation in a mammal caused by specific binding of ICAM-3 present on T cells of the mammal with DC-SIGN receptor present on dendritic cells of the mammal, wherein the method comprises administering to the mammal an amount of a DC-SIGN modulator sufficient to substantially modulate the binding of ICAM-3 present on T cells of the mammal with DC-SIGN receptor present on dendritic cells of the mammal to thereby prevent or treat inflammation.

In another aspect the invention provides a method of preventing or treating inflammation in a mammal caused by specific binding of ICAM-3 present on T cells of the mammal with DC-SIGN receptor present on dendritic cells of the mammal, wherein the method comprises administering to the mammal an amount of a DC-SIGN blocker sufficient to substantially inhibit the binding of ICAM-3 present on T cells of the mammal with DC-SIGN receptor present on dendritic cells of the mammal to thereby prevent or treat inflammation. In a preferred embodiment the DC-SIGN blocker comprises a binding moiety of the Dengue virus E glycoprotein. In another preferred embodiment the mammal is a human.

In a further aspect the invention provides a pharmaceutical composition comprising:
  a) A DC-SIGN modulator, and
  b) at least one pharmaceutically acceptable excipient;
    wherein the DC-SIGN modulator is present in the composition at an achievable therapeutic concentration.

In another aspect the invention provides a pharmaceutical composition comprising:
  c) A DC-SIGN blocker, and
  d) at least one pharmaceutically acceptable excipient;
    wherein the DC-SIGN blocker is present in the composition at an achievable therapeutic concentration.

In some embodiments of the pharmaceutical composition the DC-SIGN blocker is a derivative of a viral effector molecule. In one embodiment DC-SIGN blocker comprises the binding moiety of a Dengue virus effector molecule. In another embodiment the Dengue virus effector molecule is Dengue virus E glycoprotein.

In other embodiments of the pharmaceutical composition the DC-SIGN blocker is an antibody. Embodiments where the DC-SIGN blocker is an antibody include embodiments where the antibody is a monoclonal antibody; the monoclonal antibody is humanized; the antibody specifically binds DC-SIGN; the monoclonal antibody is Mab 1B10.2.6; the antibody specifically binds the viral effector molecule; or the antibody specifically binds the binding moiety of the viral effector molecule.

In a further aspect the invention provides a method of identifying a DC-SIGN modulator, wherein the method comprises:
  a) determining a baseline binding value by:
    i. providing cultured cells comprising a DC-SIGN receptor;
    ii. exposing the cultured cells to a marked viral effector molecule binding moiety for a period of time sufficient to allow binding equilibrium to be reached; and
    iii. determining the extent of binding of the marked viral effector molecule binding moiety to the cultured cells to thereby determine a baseline binding value;

b) determining a test substance binding value by:
  i. providing cultured cells comprising a DC-SIGN receptor
  ii. exposing the cultured cells to a marked viral effector molecule binding moiety in the presence of a test substance for a period of time sufficient to allow binding equilibrium to be reached; and
  iii. determining the extent of binding of the marked viral effector molecule binding moiety to the cultured cells to thereby determine a test substance binding value; and
c) determining a test substance binding modulation value for the test substance by dividing the test substance binding value by the baseline binding value,
wherein a test substance binding inhibition value representing an about 95% modulation of binding of the viral effector molecule to dendritic cells by the test substance, indicates that the test substance is a substance that substantially modulates the binding of a viral effector molecule to the DC-SIGN receptor.

In a preferred aspect the invention provides a method of identifying a DC-SIGN blocker, wherein the method comprises:
a) determining a baseline binding value by:
  i. providing cultured cells comprising a DC-SIGN receptor;
  ii. exposing the cultured cells to a marked viral effector molecule binding moiety for a period of time sufficient to allow binding equilibrium to be reached; and
  iii. determining the extent of binding of the marked viral effector molecule binding moiety to the cultured cells to thereby determine a baseline binding value;
b) determining a test substance binding value by:
  i. providing cultured cells comprising a DC-SIGN receptor;
  ii. exposing the cultured cells to a marked viral effector molecule binding moiety in the presence of a test substance for a period of time sufficient to allow binding equilibrium to be reached; and
  iii. determining the extent of binding of the marked viral effector molecule binding moiety to the cultured cells to thereby determine a test substance binding value; and
c) determining a test substance binding inhibition value for the test substance by dividing the test substance binding value by the baseline binding value,
wherein a test substance binding inhibition value representing an about 95% inhibition of binding of the viral effector molecule to dendritic cells by the test substance, indicates that the test substance is a substance that substantially inhibits the binding of a viral effector molecule to the DC-SIGN receptor.

The method of identifying a DC-SIGN blocker includes embodiments where the cultured cells are DC; the cultured cells are THP-1 cells; the viral effector molecule is a Dengue virus effector molecule; and the Dengue virus effector molecule is Dengue virus E glycoprotein.

In a further aspect the invention provides an isolated DC-SIGN blocker identified by the above method of identifying a DC-SIGN blocker.

In another aspect the invention provides a method of targeting a subject molecule to a cell expressing a DC-SIGN receptor by exposing the cell to a targeting complex, where the targeting complex comprises a subject molecule and a DC-SIGN blocker, and where the exposure is under conditions which allow the DC-SIGN blocker to bind to DC-SIGN on the cell expressing the DC-SIGN receptor, thereby targeting the subject molecule to the cell expressing a DC-SIGN receptor.

The method of targeting a subject molecule to a cell expressing a DC-SIGN receptor includes embodiments where the DC-SIGN blocker is an antibody; the DC-SIGN blocker is a monoclonal antibody; the subject molecule is a protein; the subject molecule is an antibody; the subject molecule is labeled; the exposure occurs in vivo; and the exposure occurs in vitro.

BRIEF DESCRIPTION OF THE DRAWINGS

The invention will be more fully described with reference to the drawings in which:

FIG. 3 shows that Anti-DC-SIGN Mab 1B10.2.6 blocks DEN-1 virus infection of human DCs. Prior to infection, DCs were incubated with anti-DC-SIGN Mab 110 (20 µg/ml) or anti-DEN E Mab 9D12 (dilution 1:50) (Després et al. *Virology*, 196: 209-219, 1993) for 20 min. Antibody-treated DCs were infected with DEN-1 virus strain FGA/NA did in the presence of Mab for 2 hrs. Viral antigens were detected by indirect immunofluorescence as described in the legend of FIG. 1. The percentages of infected DCs 42 h post-infection are indicated.

DETAILED DESCRIPTION OF THE INVENTION

Figure 1:
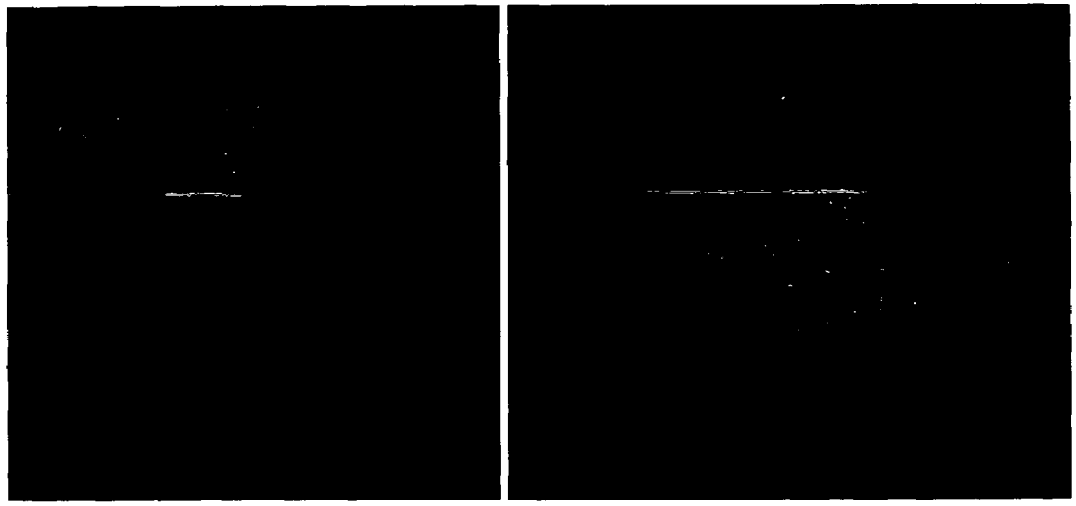
FIG. 1 depicts DEN-1 virus infection of human DCs ex-vivo. DCs infected with DEN-1 virus strain FGA/NA did (5 Ap61 FFU/cell) were fixed with 3% PFA in PBS 40 h post-infection and permeabilized with 0.1% Triton X-100 in PBS. Intracellular DEN proteins were visualized with ant-DEN-1 virus HMAF by indirect immunofluorescence and nuclei were stained with Hoescht 33258. DEN virus-infected DCs (viral antigens) and chromatin condensation (apoptotic nuclei) were observed by fluorescence. Apoptotic DCs are indicated (narrows).
Figure 1:
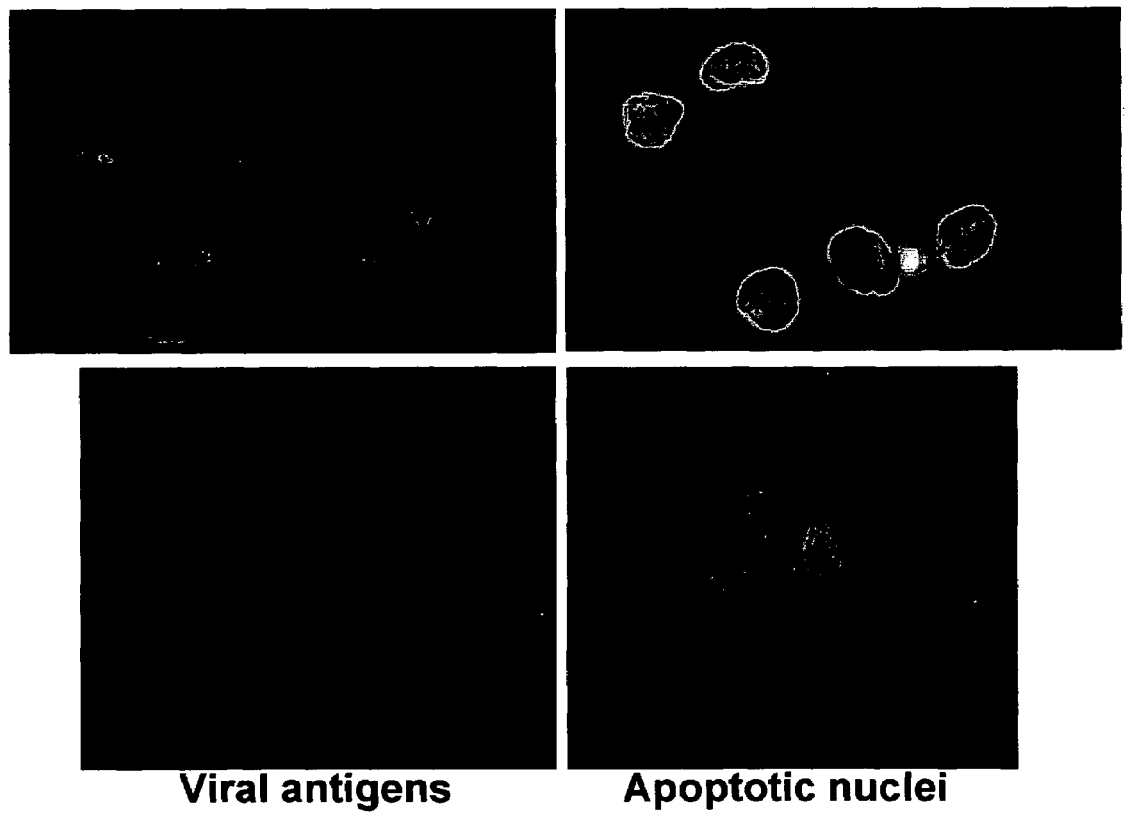

This invention relates to a method of preventing or treating a disease of a mammal, where at least one symptom of the disease is mediated at least in part by the binding of an effector molecule to a DC-SIGN receptor of the mammal to be treated. The method comprises administering to the mammal an amount of a DC-SIGN blocker sufficient to substantially inhibit the binding of the effector molecule to the DC-SIGN receptor to thereby prevent or treat the disease.

"Mammal" for purposes of the invention refers to any animal classified within the class mammalia. Nonlimiting examples of mammals include: humans and simians; pet animals, such as dogs, cats, ferrets, and guinea pigs; farm animals, such as pigs, cows, horses, sheep, goats, and llamas; and zoo animals, such as bears, zebras, elephants, and water buffalo. The mammal is preferably human.

As used herein a "disease" is any pathological condition of a mammal, which results, for example, from infection, genetic defect, or exposure to a substance in the environment. The methods and compositions of the invention are useful for preventing or treating diseases that are characterized in that at least one symptom of the disease is mediated at least in part by the binding of an effector molecule to the DC-SIGN receptor present on cells such as dendritic cells or alveolar macrophages of the mammal. Specific examples of such diseases include viral infection. A specific examples of viral infections that can be treated by the method is Dengue virus infection of a human.

In the case of humans "DC-Specific ICAM-Grabbing Non-integrin receptor" or "DC-SIGN receptor" refers generically to DC-SIGN (described in Curtis et al., 1992) and/or DC-SIGNR (described in Pohlmann et al., 2001.), and/or a homologue of DC-SIGN or DC-SIGNR. One of skill in the art will recognize that there may be some situations in which use of one or the other of these forms of DC-SIGN receptor is preferable or even necessary. One of skill in the art will recognize that human DC-SIGN protein can be obtained from many sources. For example, human DC-SIGN can be purified from human dendritic cells which are obtained from an in vivo source, such as human blood, or purified from an in vitro source, such as human dendritic cells produced in tissue culture from human dendritic cell precursor cells. It is also possible to express human DC-SIGN using a recombinant system, using either cultured dendritic cell as a host or a suitable heterologous cell type, such as COS-7 or HeLa cells, or bacteria such as E. coli.

In the case of nonhuman mammals, "DC-SIGN receptor" refers to homologues of a human DC-SIGN receptor. One of skill in the art will recognize that such proteins may be identified in any of a number of different ways. These include expression cloning, polymerase chain reaction using degenerate oligonucleotide primers, and low stringency screening of a bacterial or bacteriophage library.

Dendritic cells are a diverse population of morphologically similar cell types found in lymphoid or non-lymphoid tissues. Dendritic cells function as antigen-presenting cells that efficiently capture antigens in the peripheral tissues and process them to form MHC-peptide complexes. Dendritic cells are also involved in the early activation of non-MHC-restricted γδ and CDI-restricted T cells specific for various mycobacterial glycolipids, including CAM (Kaufmann, 2001 and Moody, et al., 2000). After antigen uptake, these immature dendritic cells acquire the unique capacity to migrate from the periphery to the T cell areas of the secondary lymphoid organs. Dendritic cells convert antigens from foreign cells and infectious microorganisms into short peptides that are bound to membrane proteins of the major histocompatibility complex (MHC). These MHC-peptide complexes are formed intracellularly but are ultimately presented on the plasma membrane where they serve as ligands for antigen-specific T cell receptors (TCR). In addition to TCR ligand formation, dendritic cells carry out many other functions, which allow them to control immunity at several points (Steinman, 2000).

Alveolar macrophages and dendritic cells are examples of cells expressing a DC-SIGN receptor. Endothelial cells are an example of cells expressing DC-SIGNR.

One of skill in the art will appreciate that dendritic cells may be obtained from an in vivo source, such as the blood of a mammal, or grown in vitro, by culturing dendritic cell precursor cells under appropriate conditions. Dendritic cell precursor cells include monocytes prepared according to Example 2.

An "effector molecule" is any molecule that specifically binds to the DC-SIGN receptor present on cells of a mammal, such as the dendritic cells or the alveolar macrophages of a mammal, and thereby mediates a symptom that is associated with a disease of that mammal. Examples of effector molecules are ligands present on viruses that bind to receptors on cells of a mammal and thereby facilitate the entry of the virus into a cell of the mammal. In cases where the effector molecules are ligands present on viruses the effector molecules can be referred to as "viral effector molecules." Examples of this type of ligand include gp120 of HIV and glycoprotein E of Dengue virus, which bind with the DC-SIGN receptor present on cells such as dendritic cells or alveolar macrophages of a human to facilitate, in the case of Dengue virus, virus entry into DC-SIGN expressing cells. Dengue virus E glycoprotein is thus a "Dengue virus effector molecule." Other types of effector molecules are ligands that are endogenous to the mammal. This type of ligand includes both ligands that are bound to the surface of other cells of the mammal and soluble ligands, which may be localized to the extracellular space of a particular tissue or circulating systemically.

A "symptom" is any pathological manifestation of the disease to be treated. A symptom is caused at least in part by the binding of an effector molecule to the DC-SIGN receptor present on the dendritic cells of the mammal to be treated if a modulation (a reduction or an increase) in the binding of the effector molecule to a the DC-SIGN receptor causes a determinable reduction in the occurrence or severity of the symptom, or both. In a preferred embodiment of the invention the symptom is no longer present or is prevented from occurring following the reduction in the binding of the effector molecule to the DC-SIGN receptor.

An effector molecule is said to "specifically bind" to the DC-SIGN receptor present on cells such as the dendritic cells or the alveolar macrophages of the mammal to be treated if such binding is not competitively inhibited by the presence of unrelated molecules (e.g., fetal calf serum), but is inhibited by antibodies to DC-SIGN (e.g., 1B10.2.6) and/or additional effector molecule.

Figure 5:
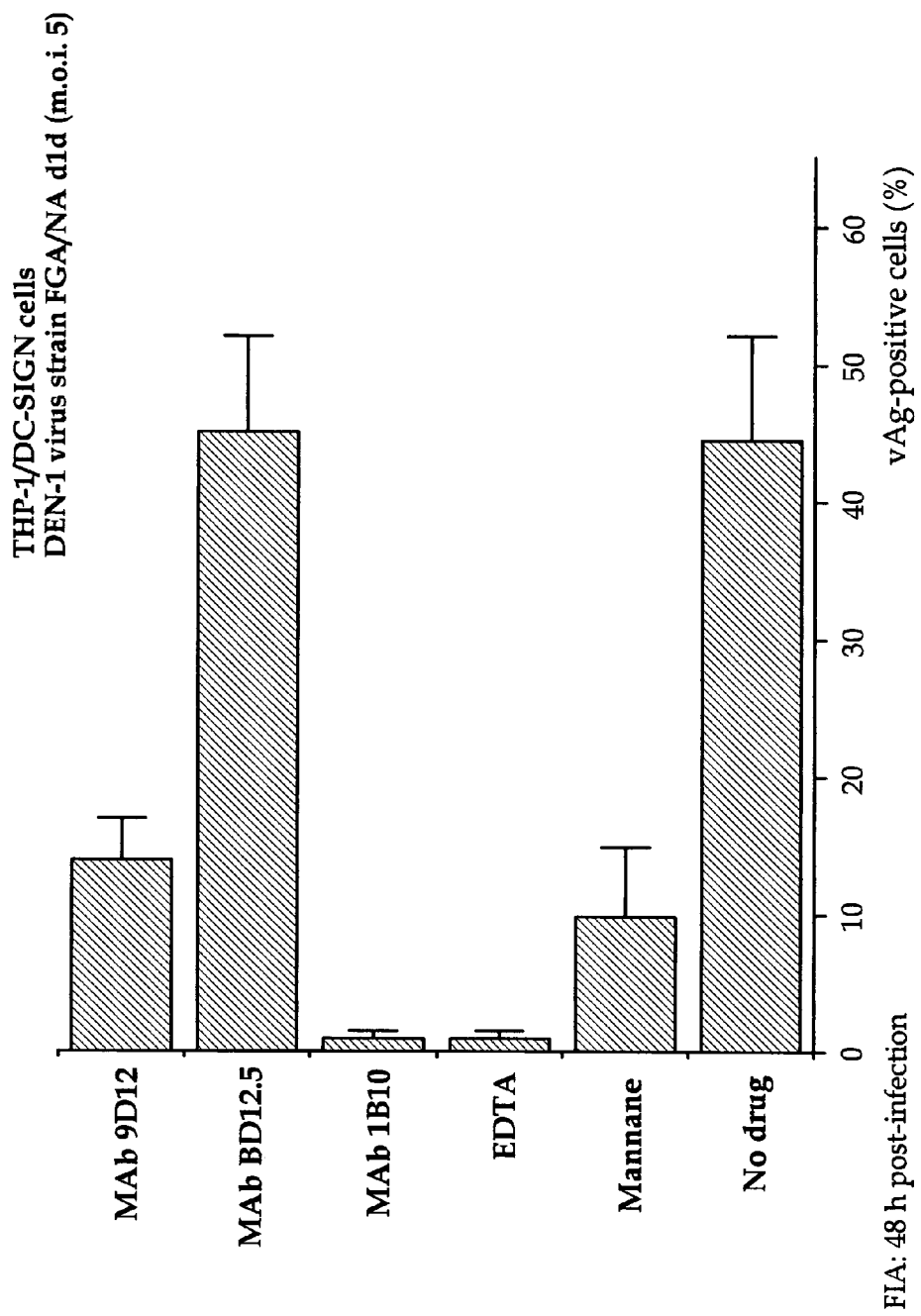
FIG. 5 shows that Mannan, EDTA and antibody specific DC-SIGN block DEN-1 virus infection of THP-1/DC/SIGN cells. Prior to infection, THP-1/DC/SIGN cells were incubated with either Mab 9D12 (dilution 1:50), Mab BD12.5 (20 µg/ml), Mab 1B10.2.6 (20 µg/ml), EDTA (5 mM), mannan (20 µg/ml), or mock-treated (control). Treated cells were infected with DEN-1 virus strain FGA/NA did (5 AP61 FFU/cell) in the presence of reagents for 2 hrs. Viral antigens were detected by indirect immunofluorescence as described in the legend of FIG. 1. The percentages of infected cells 48 h post-infection are indicated. Values represent the mean of triplicate assays ±SD.

An example of an effector molecule that specifically binds to the DC-SIGN receptor present on cells such as the dendritic cells or the alveolar macrophages of a mammal to be treated is Dengue virus E glycoprotein. The binding of E glycoprotein present on the surface of Dengue virus to DC-SIGN is not inhibited by 0.2% bovine serum albumin as shown in FIGS. 3 and 5. However, binding is inhibited by either antibody specific to DC-SIGN as shown in FIGS. 3 and 5, or soluble mannan added to the media as shown in FIG. 5, or EDTA added to the media as shown in FIG. 5.

One of skill in the art will appreciate that these assays may be used to identify other effector molecules that specifically bind to the DC-SIGN receptor present on cells such as dendritic cells of a mammal to be treated. It will also be clear to one of skill in the art that other equivalent assays may be substituted for those specifically disclosed in the Examples.

Once an effector molecule is known to specifically bind to the DC-SIGN receptor the binding of the effector molecule to DC-SIGN can be referred to simply as "binding." It will be understood by one of skill in the art that such binding is specific. In this regard, the "modulation" of binding may be discussed. Modulation can include "inhibition" or "enhancement".

"Modulation" means the act of regulating. It includes the act of inducing variations of a property of a molecule. In the context of the present invention, "modulation" means the act of regulating and varying the binding of effector molecules to their receptors. This modulation may serve to either inhibit or enhance binding, or to impose other regulatory controls.

In the context of the present invention "inhibition" of binding means a reduction in the total amount of effector molecule that binds to DC-SIGN over a fixed period of time. Inhibition of binding of the effector molecule is achieved by providing a DC-SIGN blocker. A "DC-SIGN blocker" is any molecule that substantially inhibits the binding of a given effector molecule at a concentration at which the effector molecule specifically binds to DC-SIGN. In a preferred embodiment, the DC-SIGN blocker used is a monoclonal antibody that specifically binds DC-SIGN. In another preferred embodiment the DC-SIGN blocker used comprises a binding moiety of the Dengue virus E glycoprotein.

In the context of the present invention "enhancement" of binding means an increase in the total amount of effector molecule that binds to DC-SIGN over a fixed period of time. Enhancement of binding of the effector molecule is achieved by providing a DC-SIGN enhancer. A "DC-SIGN enhancer" is any molecule that substantially enhances the binding of a given effector molecule at a concentration at which the effector molecule specifically binds to DC-SIGN.

A "binding moiety" is that portion of a molecule that substantially retains the ability to bind to a second molecule when other portions of the molecule are removed or modified or when the binding moiety is placed into a heterologous context. For example, in the case of an effector molecule as defined herein, a binding moiety of the effector molecule can be defined. A binding moiety of an effector molecule is that portion of the effector molecule that substantially retains the ability to bind to DC-SIGN when other portions of the molecule are removed or modified or when the binding moiety is placed into a heterologous context. In this context, "substantially retains" can be defined by one of skill based on the specific properties of the binding moiety that are sought.

"Substantially inhibit" means greater than 80% inhibition, greater than 90% inhibition, greater than 95% inhibition, or greater than 99% inhibition. In a preferred embodiment of the present invention about 90% binding inhibition is obtained.

"Inhibition" is measured by comparing the extent of effector molecule binding to DC-SIGN in the presence of a DC-SIGN blocker with the extent of effector molecule binding to DC-SIGN in the absence of a DC-SIGN blocker. The ratio of extent of binding in the presence of the DC-SIGN blocker compared to the extent of binding in the absence of the DC-SING blocker is then determined. The percent inhibition is then the proportional reduction in the amount of binding. For example, a ratio of 0.1 represents a 90% reduction in binding.

The term "treat," "treating" or "treatment" refers to the administration of therapy to an individual who already manifests at least one symptom of a disease. Such an individual includes an individual who is diagnosed as having a known disease.

The term "prevent," "preventing" and "prevent" refers to the administration of therapy on a prophylactic or preventative basis to an individual who may ultimately acquire the disease but who has not yet done so (i.e., those needing preventative measures). Such individuals may be identified on the basis of risk factors that are known to correlate with the subsequent occurrence of the disease.

The term "therapeutic benefit" refers to an improvement of at least one symptom of a disease, a slowing of the progression of a disease, as manifested by a slowing in the increase in severity of at least one symptom of a disease, or a cessation in the progression of at least one symptom of a disease. The therapeutic benefit is determined by comparing a symptom of a disease before and after a DC-SIGN blocker is administered.

The term "antibody" refers to any antibody that can be made by any technique known in the art. Suitable antibodies are obtained by immunizing a host animal with peptides comprising all or a portion of the target protein. Suitable host animals include mouse, rat sheep, goat, hamster, rabbit, etc. The origin of the protein immunogen may be mouse, human, rat, monkey, or microorganism such as a bacteria or virus etc. The host animal will generally be a different species than the immunogen, e.g. human protein used to immunize mice, etc.

The immunogen may comprise the complete protein, or fragments and derivatives thereof. Preferred immunogens comprise all or a part of one of the subject proteins, where these residues contain the post-translation modifications, such as glycosylation, found on the native target protein. Immunogens comprising the extracellular domain are produced in a variety of ways known in the art, e.g. expression of cloned genes using conventional recombinant methods, isolation from tumor cell culture supernatants, etc.

For preparation of polyclonal antibodies, the first step is immunization of the host animal with the target protein, where the target protein will preferably be in substantially pure form, comprising less than about 1% contaminant. The immunogen may comprise the complete target protein, fragments or derivatives thereof. To increase the immune response of the host animal, the target protein may be combined with an adjuvant, where suitable adjuvants include alum, dextran, sulfate, large polymeric anions, oil & water emulsions, e.g. Freund's adjuvant, Freund's complete adjuvant, and the like. The target protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The target protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against a mouse protein, the animal will generally be a hamster, guinea pig, rabbit, etc. The antibody may be purified from the hybridoma cell supernatants or ascites fluid by conventional techniques, e.g. affinity chromatography using protein according to the subject invention bound to an insoluble support, protein A sepharose, etc.

The antibody may be produced as a single chain, instead of the normal multimeric structure. Single chain antibodies are described in Jost et al. (1994) *J.B.C.* 269:26267-73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Also provided are "artificial" antibodies, e.g., antibodies and antibody fragments produced and selected in vitro. In some embodiments, such antibodies are displayed on the surface of a bacteriophage or other viral particle. In many embodiments, such artificial antibodies are present as fusion proteins with a viral or bacteriophage structural protein, including, but not limited to, M13 gene III protein. Methods of producing such artificial antibodies are well known in the art. See, e.g., U.S. Pat. Nos. 5,516,637; 5,223,409; 5,658,727; 5,667,988; 5,498,538; 5,403,484; 5,571,698; and 5,625,033.

For in vivo use, particularly for injection into humans, it is desirable to decrease the antigenicity of the antibody. An immune response of a recipient against the blocking agent will potentially decrease the period of time that the therapy is effective. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *P.N.A.S.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

In yet other embodiments, the antibodies may be fully human antibodies. For example, xenogeneic antibodies which are identical to human antibodies may be employed. By xenogenic human antibodies is meant antibodies that are the same has human antibodies, i.e. they are fully human antibodies, with exception that they are produced using a non-human host which has been genetically engineered to express human antibodies. See e.g. WO 98/50433; WO 98,24893 and WO 99/53049, the disclosures of which are herein incorporated by reference.

Antibody fragments, such as Fv, $F(ab')_2$ and Fab may be prepared by cleavage of the intact protein, e.g. by protease or chemical cleavage. Alternatively, a truncated gene is designed. For example, a chimeric gene encoding a portion of the $F(ab')_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc An example of a disease that can be prevented or treated utilizing the present invention is Dengue virus infection. The results presented in the examples demonstrate for the first time a role for DC-SIGN in Dengue virus binding to human dendritic cells.

The results described herein, including the results described in the examples, show that highly purified DEN-1 virus bearing mosquito N-linked oligosaccharides is able to replicate in human DC and produce progeny virus. Apoptotic cell death was also observed among DEN-1 virus-infected DCs. The C-lectin molecule, DC-SIGN, is expressed at the surface of DCs. The experiments described herein sought to determine whether the DC-specific adhesion receptor DC-SIGN has the ability to promote DEN virus infection of human DC cells. The results showed that DC-SIGN specific antibody has a blocking action at the level of DEN-1 virus infection. A novel function of DC-SIGN has been therefore identified as DEN virus binding protein possibly through interaction with the E glycoprotein. The process of DC-SIGN-mediated DEN virus infectivity to DCs provides a new mechanism for targetting the design of anti-viral compounds.

In accordance with these results, the invention provides a method of preventing or treating a disease of a mammal, where at least one symptom of the disease is mediated at least in part by the binding of an effector molecule to a DC-SIGN receptor of the mammal to be treated, and where the method comprises administering to the mammal an amount of a DC-SIGN blocker sufficient to substantially inhibit the binding of the effector molecule to the DC-SIGN receptor to thereby prevent or treat the disease.

In some embodiments the DC-SIGN blocker is a blocking derivative of the effector molecule. In other embodiments the DC-SIGN blocker is an antibody.

Among embodiments of the invention where the DC-SIGN blocker is an antibody are included embodiments where the antibody specifically binds DC-SIGN and embodiments where the antibody specifically binds the effector molecule.

In some embodiments the DC-SIGN blocker is a mannosylated molecule that binds to a DC-SIGN receptor. The mannosylated molecule may be mannan.

The invention also provides a method of preventing or treating a viral infection of a mammal, where the viral infection is mediated at least in part by the binding of a viral effector molecule to a DC-SIGN receptor of the mammal to be treated, where the method comprises administering to the mammal an amount of a DC-SIGN blocker sufficient to substantially inhibit the binding of the viral effector molecule to the DC-SIGN receptor to thereby prevent or treat the viral infection.

In some embodiments of the method the DC-SIGN blocker comprises a binding moiety of the viral effector molecule. In other embodiments the DC-SIGN blocker comprises a binding moiety of a viral envelope glycoprotein. In other embodiments the DC-SIGN blocker is an antibody. The antibody may specifically bind DC-SIGN or specifically bind the viral effector molecule. In additional embodiments the DC-SIGN blocker is a mannosylated molecule that binds to a DC-SIGN receptor. The mannosylated molecule may be mannan.

Among embodiments of the invention in which the DC-SIGN blocker is an antibody are included embodiments in which the antibody is a monoclonal antibody; the mammal is a human and the antibody is a monoclonal antibody that is humanized; the antibody specifically binds DC-SIGN; the monoclonal antibody is Mab 1 B10.2.6; the antibody specifically binds the viral effector molecule; and the antibody specifically binds the binding moiety of the viral effector molecule.

In further embodiments of the method the viral effector molecule is a molecular constituent of the viral envelope. In certain embodiments the molecular constituent of the viral envelope is an envelope glycoprotein.

In additional embodiments of the method the DC-SIGN blocker comprises a binding moiety of the viral effector molecule. In some embodiments of the invention in which the viral effector molecule is a molecular constituent of the viral envelope the DC-SIGN blocker that is used comprises a binding moiety of the envelope glycoprotein.

In a preferred embodiment, the viral infection is a Flaviviridae infection and the viral effector molecule is a Flaviviridae effector molecule. In a more preferred embodiment, the viral infection is a Dengue virus infection and the viral effector molecule is a Dengue virus effector molecule. In a further preferred aspect the mammal is a human. In some embodiments the Dengue virus effector molecule is a molecular constituent of the Dengue virus envelope. In further embodiments the molecular constituent of the Dengue virus envelope is a Dengue virus envelope glycoprotein. In yet further embodiments the Dengue virus envelope glycoprotein is Dengue virus E glycoprotein.

Included among embodiments of the invention in which the viral infection is a Dengue virus infection and the viral effector molecule is a Dengue virus effector molecule are embodiments where the DC-SIGN blocker comprises a binding moiety of the Dengue virus effector molecule; the DC-SIGN blocker comprises a binding moiety of the Dengue virus E glycoprotein; the DC-SIGN blocker is a recombinantly produced protein; and the DC-SIGN blocker is an antibody. Among embodiments where the DC-SIGN blocker is an antibody are embodiments where the antibody is a monoclonal antibody; the mammal is a human and the monoclonal antibody is humanized; the antibody specifically binds DC-SIGN; the monoclonal antibody is Mab 1B10.2.6; and the antibody specifically binds the Dengue virus effector molecule. Among embodiments where the antibody specifically binds the Dengue virus effector molecule are embodiments where the Dengue virus effector molecule is Dengue virus E glycoprotein.

In a preferred embodiment of the invention the effector molecule and the DC-SIGN blocker are the same. In a second preferred embodiment the effector molecule and the DC-SIGN blocker are different.

It is interesting that both Dengue virus and HIV (as well as SIV) can bind to DC-SIGN. HIV binding to dendritic cells is mediated by the binding of the gp120 glycoprotein of HIV with DC-SIGN. Thus, gp120 is a viral effector molecule. The invention thus provides a method for the prevention and treatment of HIV infection. Specifically, it is an object of the invention to provide a method of preventing or treating an HIV or SIV infection of a human or a simian. The method comprises administering to the human or simian an amount of a DC-SIGN blocker that is sufficient to inhibit the interaction of HIV or SIV with DC-SIGN receptor present on dendritic cells of the human or simian to thereby prevent or treat the HIV or SIV infection.

DC-SIGN is also believed to have a critical role in mediating the known loose adhesion that takes place between dendritic cells and T cells in the apparent absence of foreign antigen. This adhesion is thought to be necessary to provide an opportunity for the TCR to scan the dendritic cell surface and identify the very small amounts of TCR ligand which are present, and in turn to become activated by this ligand. For this reason, the interaction between DC-SIGN on dendritic cells, and ICAM-3 on T cells, is likely to be critically important for the process of T cell activation and stimulation. This model suggests that the DC-SIGN-ICAM-3 interaction may have a role in mediating and/or potentiating other stimulatory effects of dendritic cells on T cells.

For this reason DC-SIGN blockers may be potent anti-inflammatory agents, by blocking the interaction of the ICAM-3 effector molecule with DC-SIGN. Accordingly, the invention also provides a method of preventing or treating inflammation in a mammal caused by interaction of ICAM-3 present on T cells of the mammal with DC-SIGN receptor present on dendritic cells of the mammal. The method comprises administering to the mammal an amount of a DC-SIGN blocker that is sufficient to inhibit the interaction of ICAM-3 present on T cells of the mammal with DC-SIGN receptor present on dendritic cells of the mammal to thereby prevent or treat inflammation.

The invention also provides pharmaceutical compositions comprising a DC-SIGN blocker. Such compositions may be suitable for pharmaceutical use and administration to patients. The compositions typically contain a purified DC- SIGN blocker at a therapeutically achievable concentration and a pharmaceutically acceptable excipient. As used herein, the phrase "pharmaceutically acceptable excipient" includes any and all solvents, dispersion media, coatings, antibacterial and antifungal agents, isotonic and absorption delaying agents, and the like, that are compatible with pharmaceutical administration. The use of such media and agents for pharmaceutically active substances is well known in the art. The compositions can also contain other active compounds providing supplemental, additional, or enhanced therapeutic functions. The pharmaceutical compositions can also be included in a container, pack, or dispenser together with instructions for administration.

A pharmaceutical composition of the invention is formulated to be compatible with its intended route of administration. Methods to accomplish the administration are known to those of ordinary skill in the art. The administration may, for example, be intravenous, intramuscular, subcutaneous, or via inhalation.

Solutions or suspensions used for subcutaneous application typically include one or more of the following components: a sterile diluent, such as water for injection, saline solution, fixed oils, polyethylene glycols, glycerin, propylene glycol or other synthetic solvents; antibacterial agents, such as benzyl alcohol or methyl parabens; antioxidants, such as ascorbic acid or sodium bisulfite; chelating agents, such as ethylenediaminetetra acetic acid; buffers, such as acetates, citrates or phosphates; and agents for the adjustment of tonicity, such as sodium chloride or dextrose. The pH can be adjusted with acids or bases, such as hydrochloric acid or sodium hydroxide. Such preparations can be enclosed in ampoules, disposable syringes or multiple dose vials made of glass or plastic.

Pharmaceutical compositions suitable for injection include sterile aqueous solutions or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, one may include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

For administration by inhalation, the DC-SIGN blocker containing compositions are delivered in the form of an aerosol spray from pressured container or dispenser, which contains a suitable propellant, e.g., a gas such as carbon dioxide, or a nebulizer.

In one embodiment, a purified DC-SIGN blocker is prepared with carriers that will protect it against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions containing LAM can also be used as pharmaceutically acceptable carriers. These can be prepared according to methods known to those skilled in the art, for example, as described in U.S. Pat. No. 4,522,811.

Therapeutically useful agents, such as growth factors (e.g., BMPs, TGF-$\beta$, FGF, IGF), cytokines (e.g., interleukins and CDFs), antibiotics, and any other therapeutic agent beneficial for the condition being treated can optionally be included in or administered simultaneously or sequentially with the DC-SIGN blocker.

It is especially advantageous to formulate compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of compositions comprising a DC-SIGN blocker can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. DC-SIGN blockers which exhibit large therapeutic indices are preferred.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any DC-SIGN blocker used in the present invention, the therapeutically effective dose can be estimated initially from cell culture assays. A dose can be formulated in animal models to achieve a circulating plasma concentration range that includes the IC50 (i.e., the concentration of the test DC-SIGN blocker which achieves a half-maximal inhibition of symptoms) as determined in cell culture. Levels in plasma can be measured, for example, by high performance liquid chromatography. The effects of any particular dosage can be monitored by a suitable bioassay.

A targeting complex of the present invention comprises at least one DC-SIGN blocker molecule covalently attached to at least one subject molecule. In some embodiments, a single DC-SIGN blocker molecule is covalently linked to a single subject molecule. In other embodiments, more than one DC-SIGN blocker molecule can be covalently linked to a single subject molecule. The multiple DC-SIGN blocker molecules can each be independently covalently linked to the subject molecule; alternatively, one or more of the more than one DC-SIGN blocker molecules can be covalently linked only to one or more other DC-SIGN blocker molecules, at least one of which is itself covalently linked to the subject molecule.

In other embodiments, multiple subject molecules are covalently linked to a single DC-SIGN blocker molecule. The multiple subject molecules can each be independently covalently linked to the DC-SIGN blocker molecule; alternatively, one or more of the more than one subject molecules can be covalently linked only to one or more other subject molecules, at least one of which is itself covalently linked to the DC-SIGN blocker molecule.

Additional embodiments of the invention utilize compositions of more than one of the various types of DC-SIGN blockers described immediately above. There is no limit to the diversity of such compositions which can be used. One of skill in the art will appreciate that the composition to be used for a particular application will be dictated by many factors and that a suitable composition can thus be appropriately chosen for each application of the invention.

Techniques for making the DC-SIGN blockers of the invention are well known and widely practiced by those of skill in the biochemistry art, and thus need not be detailed here. However, one of skill in the art will recognize that any suitable technique which results in the formation of a covalent bond between a subject molecule and a DC-SIGN blocker molecule can be used.

Subject molecules can be any molecule of interest. Non-limiting examples include: small organic molecules, proteins, nucleic acids, carbohydrates, and lipids. One of ordinary skill in the art will appreciate that any known derivatives and composites of one or more of these classes of molecules can also be used.

In the case in which the subject molecule is a protein, nucleic acid, carbohydrate, or lipid, the subject molecule can be obtained from a natural source, i.e., purified from an organism, which comprises the molecule. Alternatively, the subject molecule can be obtained from a recombinant source, i.e., from a recombinant organism, which has been engineered to produce a subject molecule of choice. In some cases, the recombinant organism that is used to produce the recombinant subject molecule is one that comprises the subject molecule, as the organism occurs in nature, in nonrecombinant form. In other cases, the subject molecule is one that does not naturally occur in the recombinant organism.

The subject molecules of the invention also include derivatives of small organic molecules, proteins, nucleic acids, carbohydrates, and lipids. As used here, a derivative is a form of small organic molecule, protein, nucleic acid, carbohydrate, or lipid that is modified from its natural state by adding, subtracting, or altering one or more chemically reactive sites present on the small organic molecule, protein, nucleic acid, carbohydrate, or lipid. Techniques for making derivatives of small organic molecules, proteins, nucleic acids, carbohydrates, and lipids are well known and widely practiced by those of skill in the biochemistry art, and thus need not be detailed here.

In a preferred embodiment the subject molecule is an antibody.

The subject molecule can also be a molecule that is antigenic. A molecule is antigenic when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

The targeting complex of the invention can be exposed to a cell expressing DC-SIGN, such as a dendritic cell either in vivo or in vitro. In vivo exposure is achieved by administering the targeting complex in a pharmaceutical composition as described herein or in any suitable equivalent formulation known in the art. In that case, the targeting complex will bind to DC-SIGN on the surface of dendritic cells in vivo. In vitro exposure occurs when dendritic cells grown in vitro are exposed to the targeting complex.

The following examples aid in describing certain aspects of the invention. One of ordinary skill in the art will recognize the numerous modifications and variations that may be performed without altering the spirit or scope of the present invention. Such modifications and variations are believed to be encompassed within the scope of the invention. The examples do not in any way limit the invention.

EXAMPLES

Example 1

*Flaviviruses*

The production and purification of DEN type-1 (DEN-1) virus strain FGA/NA d1d (GenBank accession number AF226686) (Duarte dos Santos et al., *Virology,* 274: 292, 2000) and West Nile (WN) virus strain IS-98-ST1 (GenBank accession number AF481864) (Mashimo et al., *PNAS,* 99: 11311, 2002) from mosquito *Aedes pseudoscutellaris* AP61 cell monolayers and virus titration on AP61 cells by focus immunodetection assay (FIA) were performed as previously described (Despres et al., *Virology,* 196: 209, 1993). Yellow fever (YF) virus vaccine strain 17D-204 (STAMARIL, Pasteur Vaccins, Lot E113) (GenBank accession number: X07755) was propagated twice in African green monkey kidney VERO cell monolayers, purified in sucrose gradients and titrated on VERO cells. Infectivity titers were expressed as focus forming units (FFU).

It is noteworthy that FGA/NA d1d E glycoprotein has two N-linked glycosylation sites at positions $Asn_{67}$ and $Asn_{153}$. Both N-glycosylation sites of the DEN-1 glycoprotein E appear to be utilized during the N-glycosylation process (Courageot et al., *J. Virol.,* 74: 564-572). IS-98-ST1 E glycoprotein has a single N-linked glycosylation site that appeared to be utilized (Desprès, personal communication). Whereas 17D-204 E protein is not N-glycosylated. The *flavivirus* M protein is not glycosylated.

In these experiments, we tested DEN-1 and WN virion-associated E glycoproteins which bear mature N-linked oligosaccharides from mosquito AP61 cells.

Example 2

Human Mononuclear Cells

Human DCs from purified mononuclear cells, human monocytic cell line THP-1 (ATCC TIB 202) and DC-SIGN expressing cell clone, THP/DC-SIGN, were obtained from Ali Amara (Immunologie Virale) (Kwon et al., *Immunity*, 16: 135, 2002). Immature DC, THP-1 and THP/DC-SIGN cells were cultured in RPMI 1640 culture medium supplemented with 10% heat-inactivated fetal calf serum (FCS) (Eurobio, lot 160402), 2 mM L-glutamine and antibiotics Peni/Strepto.

DC were adhered to poly-L-lysine (Sigma)-coated glass Lab-tek chambers (Nalge Nunc International) ($5 \times 10^4$ cells per cm$^2$). THP-1 and THP/DC-SIGN cells were adhered to poly-L-lysine-treated glass Lab-tek chambers or polylysine-treated 12-well flasks ($5 \times 10^4$ cells per cm$^2$).

Example 3

Virus Infections

Cells were washed once with RPMI 1640, incubated with highly purified virus in RPMI 1640 supplemented with 0.2% bovine serum albumine (BSA, pH 7.5) (Sigma) for 2 hrs at 37° C. and placed into fresh media supplemented with 2% FCS, 2 mM L-glutamine and antibiotics Peni/Strepto at 37° C. for 40 hrs.

The percentage of cells expressing viral antigen was determined using either DEN-1 virus-specific hyperimmune mouse ascites fluid (HMAF) 9801 (strain Hawaï), WN virus-specific HMAF 0801 (strain IS-98-ST1), or YF virus-specific HMAF. 9803 (strain FNV) with dilution of 1:50, by indirect immunofluorescence as previously described (Després et al., *J. Virol.*, 70: 4090, 1996).

Example 4

Inhibition of DC-SIGN-mediated Virus Binding

Adherent cells were incubated either with EDTA (5 mM), mannan (20 μg/ml), anti-DC-SIGN Mab 1B10.2.6 (20 μg/ml), anti-LMCV Mab 12.5 (isotype control, 20 μg/ml), or DEN E-specific Mab 9D12 (dilution 1:50) in RPMI 1640 supplemented with 0.2% BSA for 20 min at room temperature before binding the virus for 2 hrs. Two hours after infection, cells were washed with RPMI 1640 and incubated with RMPI 1640 2% FCS for 40 hrs. Anti-DC-SIGN Mab 1B10.2.6 and anti-LMCV Mab 12.5 were obtained from Ali Amara.

Example 5

Immunofluorescence Assay

Briefly, cells were fixed with 3% paraformaldehyde (PFA) in PBS for 20 min at room temperature, incubated with 50 mM NH$_4$Cl in PBS for 20 min and permeabilized with 0.1% Triton X-100 in PBS for 5 min. Intracellular viral antigens were stained with anti-*flavivirus* HMAF. The secondary antibody used was a FITC-conjugated goat anti-mouse IgG (Sigma). Cells were observed with a fluorescence microscope.

Example 6

In situ Detection of Apoptotic Cells

To assess the nuclear changes associated with apoptotic cell death, PFA-fixed cells on glass slides were treated with 0.1 μg/ml Hoechst 33258 (Sigma) in 0.1% citrate buffer (pH 6.0) for 10 min at room temperature. Cells were considered to be apoptotic if their nuclei exhibited margination and condensation of chromatin. Cells were observed with a fluorescence microscope.

Apoptosis-induced DNA breaks were detected by the deoxyterminal transferase-mediated dUTP nick-end labeling (TUNEL) method (Després et al., *J. Virol.*, 70:4090, 1996). A TUNEL assay was performed with streptavidin-CY™ 3 conjugate (Jackson Immunoresearch). Cells were observed with a fluorescence microscope.

Example 7

DEN Virus Infection of Human DC Ex-vivo

We have examined whether DEN-1 virus strain FGA/NA d1d replicates in DCs. Inoculation with 5 AP61 FFU/cell was needed to infect 50% of human DCs to DEN virus within the 40 hrs as examined by IF assay using anti-DEN-1 HMAF (FIG. 1). Infective particles accumulated in FGA/NA d1d-infected DCs to 9 ($\pm 3$)$\times 10^4$ APG1 FFU/ml (for 50,000 DCs) at 48 h postinfection. Unlike DEN-1 virus, lower than 1% of the DCs were infected with WN virus strain IS-98-ST1 (m.o.i. of 5 AP61 FFU/cell) or YF vaccine strain (m.o.i. of 50 VEROFFU/cell) at 40 h postinfection (data not shown).

Figure 2A:
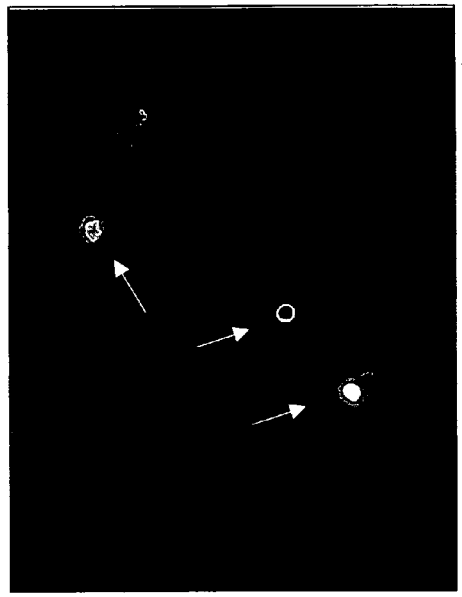
FIG. 2 depicts apoptotic DNA fragmentation in DCs infected with DEN-1 virus. Infected DCs were assayed simultaneously for the presence of DEN antigens by indirect indirect immunofluorescence (Viral antigens) as described in the legend of FIG. 1 and for apoptosis by the TUNEL assay (TUNEL). TUNEL-positive cells were observed by fluorescence. TUNEL-positive cells are indicated (narrows). Low (A) or high (B) magnification.
Figure 2A:
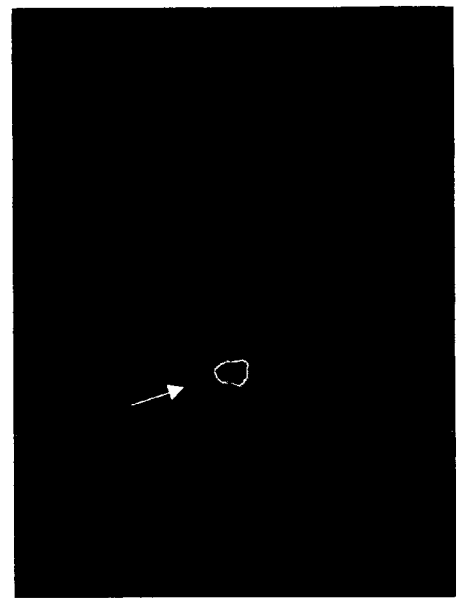
Figure 2A:
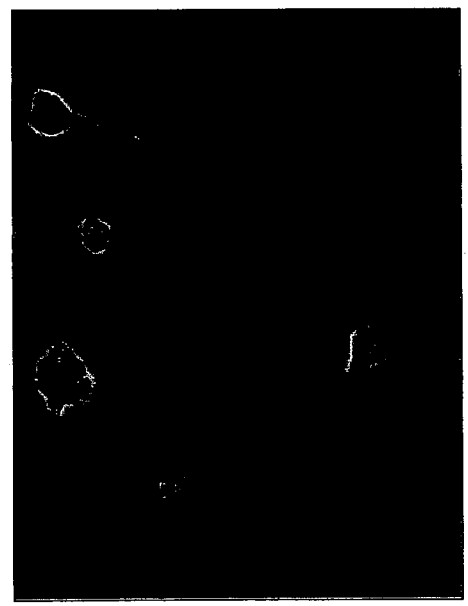
Figure 2A:
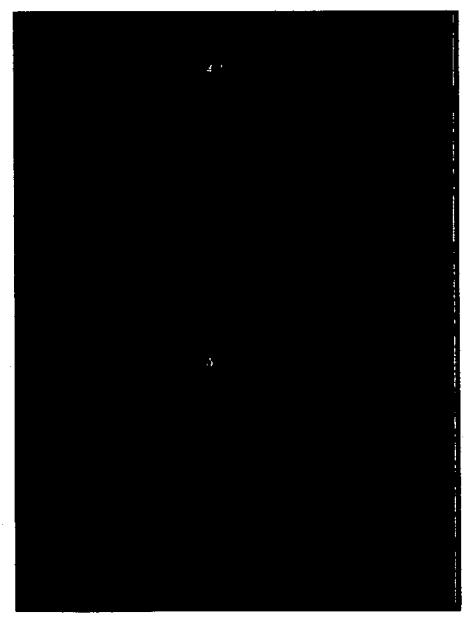
Figure 2B:
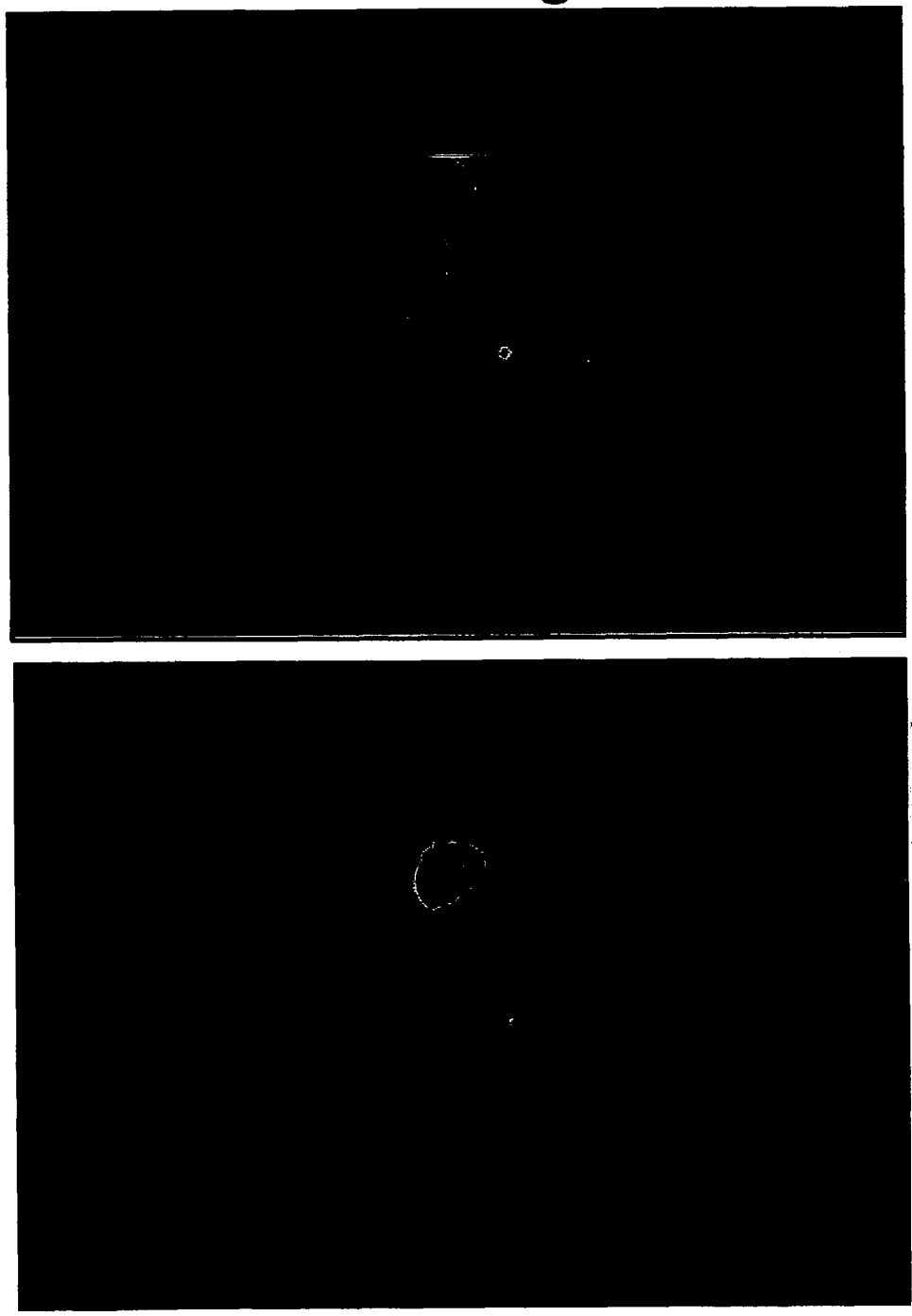

Infection of DCs with DEN-1 virus strain FGA/NA d1d results in apoptosis after 40 h of infection as judged by Hoescht 33258 staining (FIG. 1) and TUNEL method (FIG. 2A & B).

Example 8

Anti-DC-SIGN Mab 1B10.2.6 Blocks DEN-1 Virus Infection of DCs

We analyzed the effect of anti-DC-SIGN-specific Mab 1B10.2.6 on DEN-1 virus strain FGA/NA d1d infectivity. FIG. 3 indicates that 20 μg/ml of Mab 1B10.2.6 blocked FGA/NA d1d infection of DC cells as examined by IF assay. As a positive control, anti-E Mab 9D12 reduced the infectivity of DEN-1 virus by 70%. The production of infectious particles in FGA/NA d1d-infected DCs treated with Mab 1B10.2.6 was very low (<5 AP61 FFU/ml).

Example 9

DEN Virus Infection of Human Monocytes THP-1 and THP/DC-SIGN

Figure 4A:
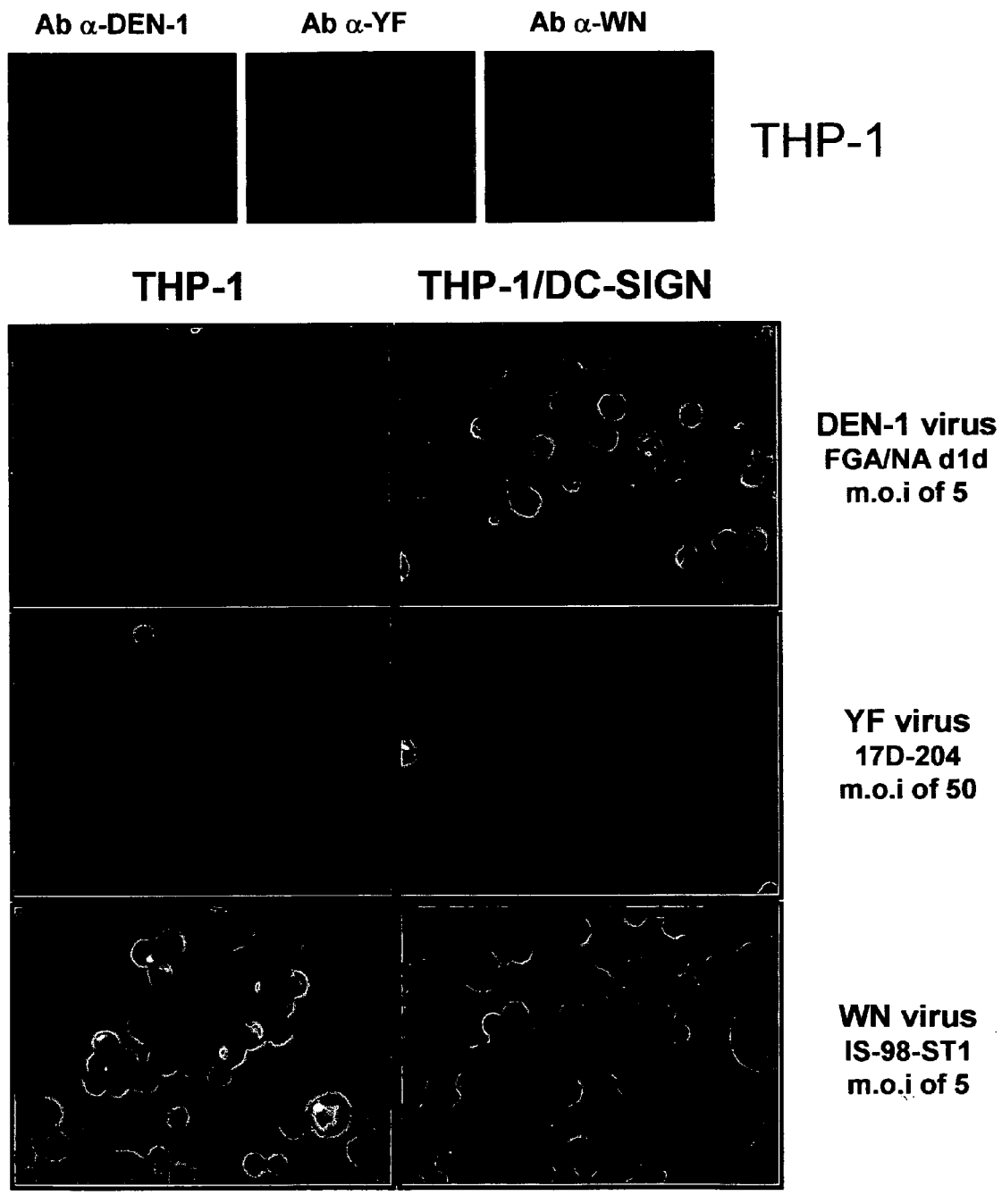
FIG. 4 depicts *Flavivirus* infections of THP-1 and THP-1/DC-SIGN cells. Cells infected with DEN-1 virus strain FGA/NA did (5 AP61 FFU/cell), YF virus strain 17D-204 (50 VEROFFU/cell), or WN virus strain IS-98-ST1 (5 AP61 FFU/cell) were assayed 40 h post-infection for the presence of viral antigens by indirect immunofluorescence as described in the legend of FIG. 1. Viral antigens were visualized with either anti-DEN-1 virus HMAF (AB α-DEN-1), anti-YF virus HMAF (AB α-YF), or anti-WN virus HMAF (Ab α-WN). (A) THP-1 cells mock-infected (top), or infected with *flavivirus* (bottom) and infected THP-1/DC cells (bottom) 40 post-infection (m.o.i., multiplicity of infection). (B) The percentages of infected cells are indicated. Values represent the mean of triplicate assays ±SD.

We further examined the specificity of the interaction between DC-SIGN and DEN virus. To investigate this issue, human monocytic THP-1 cells were first infected with DEN-1 virus strain FGA/NA d1 d. At an m.o.i of 5 AP61 FFU/cell, less than 1% of THP-1 were positive for DEN antigens as examined by IF assay (FIG. 4A & B). Similarly, YF virus vaccine strain 17D-204 (m.o.i. of 50 VEROFFU/cell) failed to replicate in THP-1 cells (FIG. 4A & B). Whereas an m.o.i of 5 AP61 FFU/cell was needed to infect about of 70% of THP-1 cells with WN virus strain IS-98-ST1 (FIG. 4A & B).

Figure 4B:
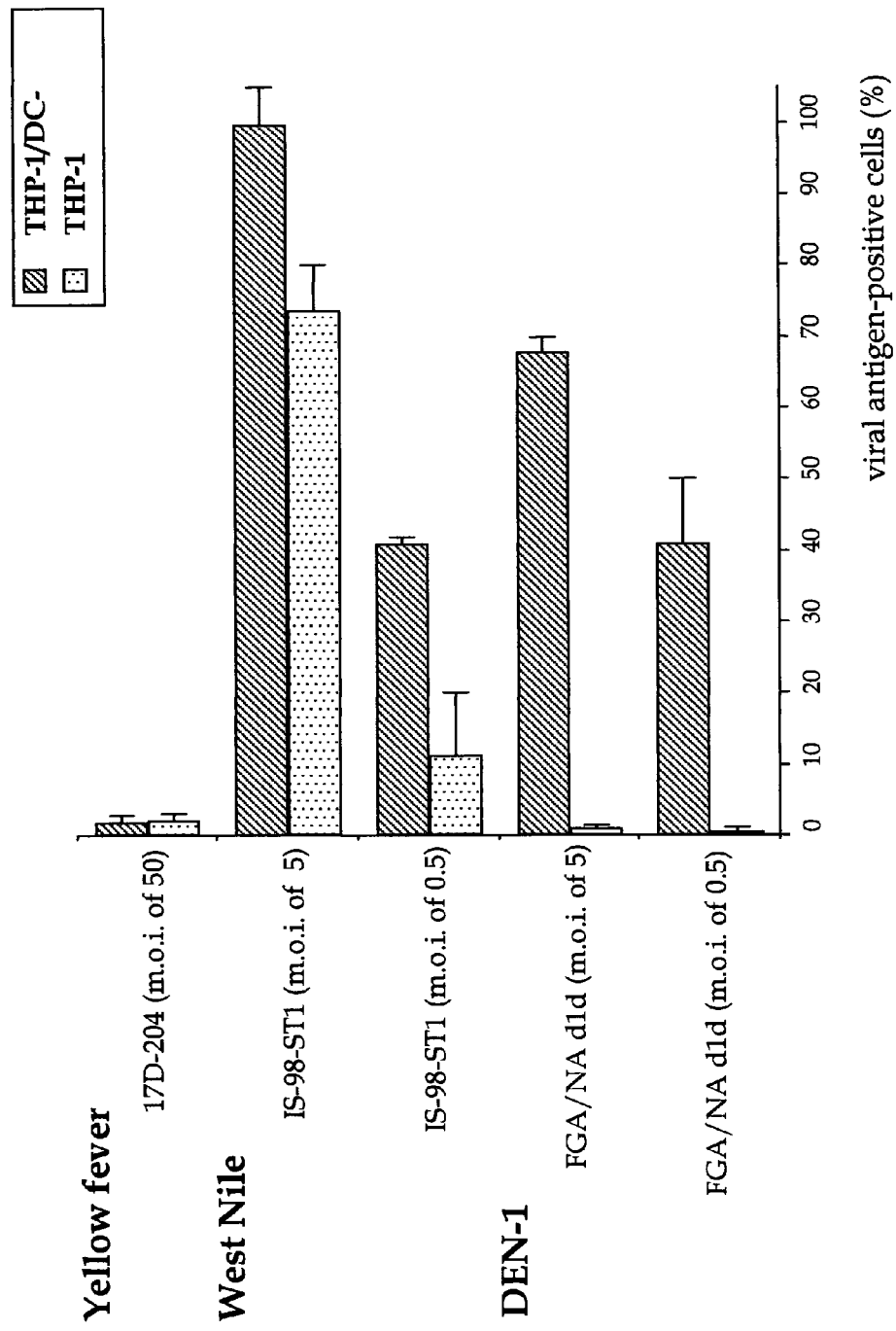

To determine whether DC-SIGN confers DEN-1 virus infectivity at THP-1, we tested the DC-SIGN-expressing human monocytic THP cell line, THP/DC-SIGN (Kwon et al., *Immunity,* 16: 135, 2002). At an m.o.i. of 5 AP61 FFU/cell, more than 50% of THP/DC-SIGN cells were positive for FGA/NA d1d antigens after 48 h of infection (FIG. 4). Mortality of THP/DC-SIGN cells in which DEN-1 virus was replicating occurred after a 96-h period of infection. Unlike DEN-1 virus, YF virus vaccine strain 17D-204 did not replicate in THP/DC-SIGN cells at an m.o.i. as high as 50 VER-OFFU/cell. It is also of interest that DC-SIGN could mediate enhancement of WN virus infection by monocytic cells (FIG. 4).

Figure 6:
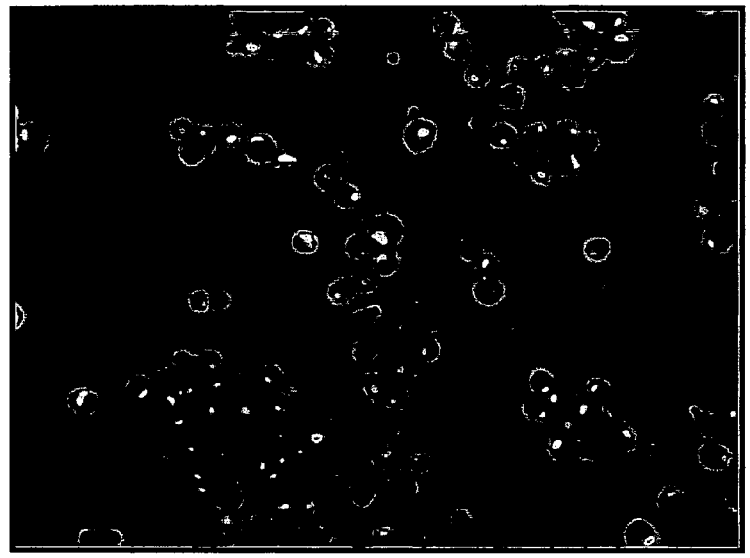
FIG. 6 depicts DEN-1 virus infection of THP-1 cell clone expressing mutant form of DC-SIGN. THP-1 Δ35 cell clone (THP-1/DC-SIGN Mutant 35) infected with DEN-1 virus strain FGH/NA did (5 AP61 FFU/cell) was assayed 40 h post-infection for the presence of viral antigens by indirect immunofluorescence as described in the legend of FIG. 1.
Figure 6:
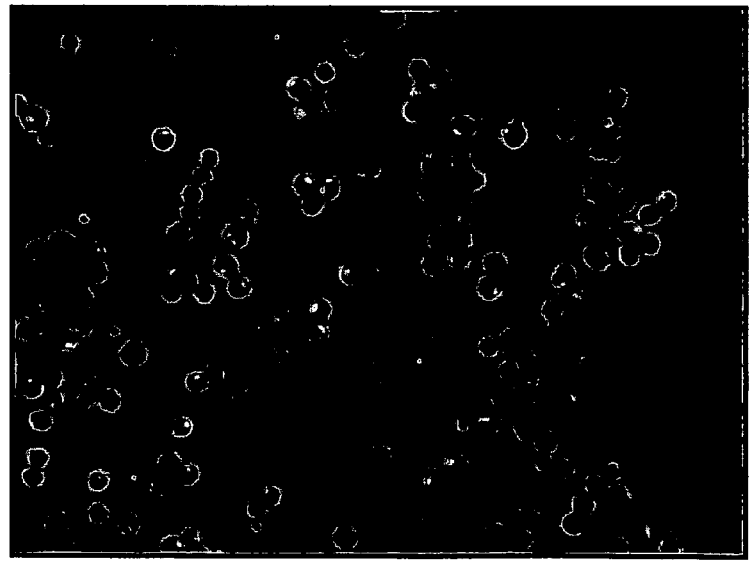

We tested the effects of mannan, ETDA and DC-SIGN specific Mab 1B10.2.6 on DC-SIGN-mediated DEN virus binding. In these experiments, Mab BD12.5 served as a negative control whereas anti-E Mab 9D12 was used as a positive control. THP/DC-SIGN cells were infected with DEN-1 virus strain FGA/NA d1d at an m.o.i. of 5 AP61 FFU/cell. When THP/DC-SIGN cells were preincubated with EDTA or DC-SIGN specific Mab 1B10.2.6, infectivity of DEN-1 virus was essentially abolished (FIG. 5). Dose of 20 μg/ml mannan was needed to reduce FGA/NA d1d infectivity by 75%. It is therefore reasonable to conclude that DC-SIGN is capable of promoting DEN virus infection of mononuclear cells The cytoplasmic tail of DC-SIGN contains two defined putative internalization motifs, a dileucine-based motif and a tyrosine-based motif. We next tested THP-1 cell clone Δ35 expressing mutant form of DC-SIGN in which the cytoplasmic domain of the molecule was truncated (Kwon et al., *Immunity,* 16: 135, 2002). The truncation removed 35 amino acids that include both the dileucine motif and the tyrosine-based motif. We found that DEN-1 virus infectivity is mostly preserved in THP-1 cell clone Δ35 (FIG. 6). Thus, the cytosolic tail does not contribute to the enhancement of DEN-1 virus infection by DC-SIGN.

DEPOSITS

The Hela cell line denoted "Hela DC-SIGN Flap" was deposited at the C.N.C.M. on Oct. 30, 2002, under the accession number I-2949.

The DC-SIGN clone denoted "DC-SIGN human clone2" was deposited at the C.N.C.M. on Oct. 30, 2002, under the accession number I-2950.

The hybridoma denoted "1B10.2.6" was deposited at the C.N.C.M. on Nov. 7, 2002, under the accession number I-2951.

REFERENCES

Bhamarapravati, N. et: al. (*Dengue and Dengue haemorrhagic fever* (1997), 367-377).
Courageot et al., *J. Virol.,* 74: 564-572.
Crooks A. J. et al. *J. Chrom.* (1990), 502, 59-68.
Crooks A. J. et al. *J. Gen. Virol.* (1994), 75, 3453-3460.
Curtus et al., *PNAS USA* (1992), 89, 8356-8360.
Després et al., *J. Virol.,* 70: 4090, 1996.
Després et al., *Virology,* 196: 209, 1993.
Drickammer, *Curr. Opin. Immunol.* 13: 585, 1999.
Duarte dos Santos et al., *Virology,* 274: 292, 2000.
Feinberg, H., Mitchell, D. A., Drickamer, K. & Weis, W. I. (2001). Structural basis for selective recognition of oligosaccharides by DC-SIGN and DC-SIGNR. *Science* 294, 2163-6.
Geijtenbeek, T. B. et al. (2000). DC-SIGN, a dendritic cell-specific HIV-1-binding protein that enhances trans-infection of T cells. *Cell* 100, 587-97.
Geijtenbeek et al., *Nature* 1: 353, 2000.
Glamand et al., *J. Virol.* (1999), 73, 6106-6110.
Gorman et al. (1982) P.N.A.S. 79:6777.
Grosschedl et al. (1985) Cell 41:885.
Hall R. A. et al., *J. Virol.* (1999), 73, 10272-10280.
Ho et al., *Immunology* 166: 1499, 2001.
Jost et al. (1994) J.B.C. 269:26267-73.
Kabat et al. (1991) Sequences of Proteins of Immunological Interest, N.I.H. publication no. 91-3242.
Kaufmann, S. H. E. (2001). How can immunology contribute to the control of tuberculosis? *Nat. Rev. Immunol.* 1, 20-30.
Kwon et al., *Immunity,* 16: 135, 2002.
Liu et al. (1987) P.N.A.S. 84:3439 and (1987) J. Immunol. 139:3521).
Marovich et al., *JID Symp. Proc.* 6: 219, 2001.
Mashimo et al., *PNAS,* 99: 11311, 2002.
Monath, T. P. et al., (1996) *Flaviviruses* in B. N. Fields, D. M. Knipe, P. M. Howly et al. (eds.) "Fields Virology" Philadelphia: Lippincott Raven Press Publishers.
Moody, D. B. et al. (2000). CD1c-mediated T-cell recognition of isoprenoid glycolipids in *Mycobacterium tuberculosis* infection. *Nature* 404, 884-8.
Okayama et al. (1983) Mol. Cell. Bio. 3:280).
Palucka, *Nat. Med* 6: 748, 2000.
Pohlmann, S., et al., *PNAS USA,* (2001), 98, 2670-2675.
Relloso et al., *J. Immunol.* 168, 2634, 2002.
Rice C. M. at al., *J. Virol.,* (1997), 71, 291-298.
Rice C. M. et al., *J. Virol.,* (1997), 71, 9608-9617).
Rice C. M. et al., *J. Virol.,* (1996), 222, 159-168.
Russel, P. K. et al. (J. Immunol., (1970), 105, 838-845).
Smith, G. W. et al. (J. Gen Virol., (1985), 66, 559-571).
Steinman, R. M. (2000). DC-SIGN: A Guide to Some Mysteries of Dendritic Cells. *Cell* 100, 491-94.
Wu et al., *Nat. Med.* 6: 816, 2000.
WO 90/10077
WO 90/04036.
WO 92/02190.
WO 98/50433.
WO 98,24893.
WO 99/53049.
U.S. Pat. No. 4,683,195.
U.S. Pat. No. 4,683,202.
U.S. Pat. No. 5,516,637.
U.S. Pat. No. 5,223,409.
U.S. Pat. No. 5,658,727.
U.S. Pat. No. 5,667,988.
U.S. Pat. No. 5,498,538
U.S. Pat. No. 5,403,484
U.S. Pat. No. 5,571,698.
U.S. Pat. No. 5,625,033.

The entire contents of all references, patents and published patent applications cited throughout this application are herein incorporated by reference in their entirety.

What is claimed is:

1. A method of inhibiting binding of a Dengue virus to a human cell, wherein the binding of the Dengue virus to the human cell is mediated at least in part by the binding of a Dengue virus effector molecule on the Dengue virus to one or more DC-SIGN receptor selected from DC-Specific ICAM-Grabbing Nonintegrin (DC-SIGN) and DC-Specific ICAM-Grabbing Nonintegrin Related (DC-SIGNR) expressed on the human cell, the method comprising:

providing to the human cell a molecule that specifically binds to the DC-SIGN receptor;

wherein the molecule that specifically binds to the DC-SIGN receptor is provided in an amount sufficient to inhibit the binding of the Dengue virus effector molecule to the DC-SIGN receptor to thereby inhibit binding of the Dengue virus to the human cell; and wherein the molecule that specifically binds to the DC-SIGN receptor is an antibody.

2. The method of 1, wherein the antibody is a monoclonal antibody.

3. The method of claim 2, wherein the monoclonal antibody is humanized.

* * * * *